United States Patent
Hirofuji et al.

(10) Patent No.: US 8,445,653 B2
(45) Date of Patent: May 21, 2013

(54) FREEZE-DRIED PREPARATION OF STABILIZED ANTHRACYCLINE COMPOUND

(75) Inventors: Hajimu Hirofuji, Oita (JP); Hotaka Hashimoto, Ibaraki (JP)

(73) Assignee: Dainippon Sumitomo Pharma, Suita-shi (JP)

( * ) Notice: Subject to any disclaimer, the term of this patent is extended or adjusted under 35 U.S.C. 154(b) by 354 days.

(21) Appl. No.: 10/536,397

(22) PCT Filed: Nov. 27, 2003

(86) PCT No.: PCT/JP03/15196
§ 371 (c)(1),
(2), (4) Date: May 26, 2005

(87) PCT Pub. No.: WO2004/050098
PCT Pub. Date: Jun. 17, 2004

(65) Prior Publication Data
US 2006/0003949 A1    Jan. 5, 2006

(30) Foreign Application Priority Data

Nov. 29, 2002 (JP) ................................ 2002-348500

(51) Int. Cl.
*C07H 15/24* (2006.01)
(52) U.S. Cl.
USPC ......................................................... 536/6.4
(58) Field of Classification Search
USPC ............................................ 514/34; 536/6.4
See application file for complete search history.

(56) References Cited

U.S. PATENT DOCUMENTS

| | | | |
|---|---|---|---|
| 4,673,668 A | 6/1987 | Ishizumi et al. | |
| 4,952,566 A | 8/1990 | Sakamaki et al. | |
| 6,376,469 B1 | 4/2002 | Shimago et al. | |
| 2004/0249137 A1 | 12/2004 | Takahashi et al. | |

FOREIGN PATENT DOCUMENTS

| | | |
|---|---|---|
| EP | 302729 A1 | 2/1989 |
| JP | 3-5397 B2 | 1/1991 |
| WO | WO-99/28331 A2 | 6/1999 |
| WO | WO-03/035660 A1 | 5/2003 |

OTHER PUBLICATIONS

USP 25/NF 20 (2002), p. 506, p. 617, p. 889 (The Pharmacopeia of the United States 25th Revision, Daunorubicin Hydrochloride for Injection (p. 506), Doxorubicin Hydrochloride for Injection (p. 617) and Idarubicin Hydrochloride for Injection (p. 889)).
Pharmaceutics, 4th Edition, p. 267, first paragraph, (1999).
16th Edition of Remington's Pharmaceutical Sciences, 1980, Mack Publishing Co., p. 1483.
Extended European Search Report dated Oct. 1, 2012, issued in the corresponding European Application No. 09845198.2. to copending U.S. Appl. No. 13/322,151.

*Primary Examiner* — Elli Peselev
(74) *Attorney, Agent, or Firm* — Birch, Stewart, Kolasch & Birch, LLP

(57) ABSTRACT

The present invention provides a lyophilized preparation of amrubicin, which contains L-cysteine or a salt thereof and has a water content of 0 to about 4% by weight within the preparation, and is stable even in a long-term storage, and further provides a method for production of said preparation. Said preparation is useful as a chemotherapeutic agent for cancers.

1 Claim, 1 Drawing Sheet

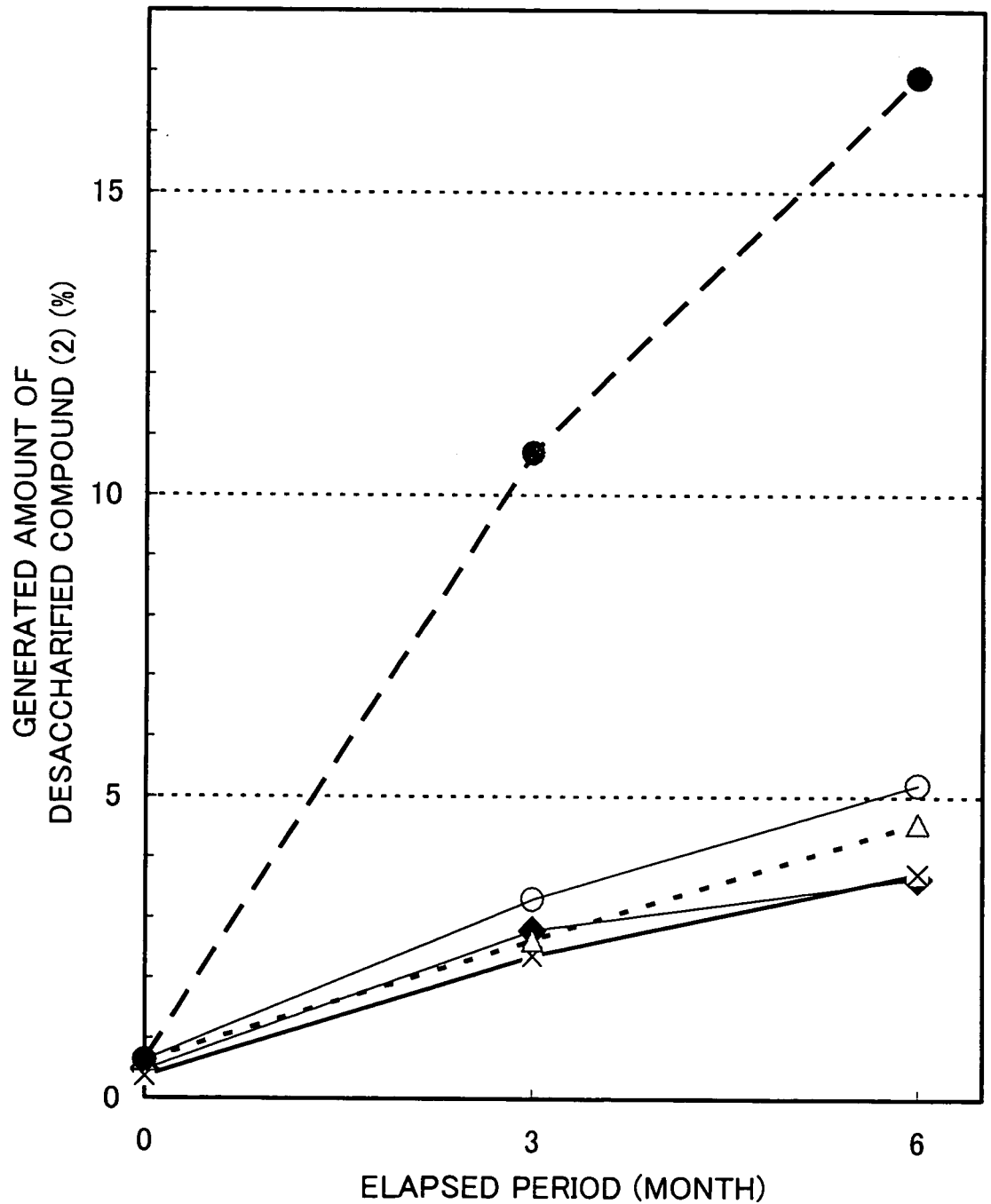

FREEZE-DRIED PREPARATION OF STABILIZED ANTHRACYCLINE COMPOUND

This application is the National Stage of International Application No. PCT/JP2003/015196, filed in the Japanese Patent Office on Nov. 27, 2003. International Application PCT/JP2003/015196 in turn claims priority under 35 USC §119(a)-(d) of Japanese Application No. 2002-348500, filed in the Japanese Patent Office on Nov. 29, 2002.

TECHNICAL FIELD

The present invention relates to a stabilized preparation of amrubicin or a salt thereof, which is useful as a chemotherapeutic agent for cancers.

BACKGROUND ART (7S,9S)-9-Acetyl-9-amino-7-[(2-deoxy-β-D-erythro-pentopyranosyl)-oxy]-7,8,9,10-tetrahydro-6,11-dihydroxy-5,12-naphthacenedione (hereinafter, referred to as amrubicin) of the following formula (1):

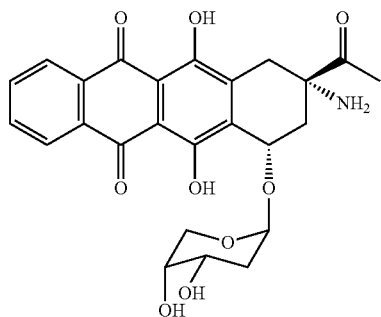

(1)

and a salt thereof have been known to be useful as a chemotherapeutic agent for cancers (see, for example, JP-B-3-5397, the corresponding U.S. Pat. No. 4,673,668). The hydrochloride of such amrubicin may have several kinds of crystal forms, and it has been known that among them, specific crystals thereof are excellently stable to heat (see, for example, Japan Patent Gazette No. 2975018, the corresponding U.S. Pat. No. 4,952,566).

Anthracycline compounds such as amrubicin are unstable in a solution state, and when formulating such a compound as an injection, it is usually formulated in the form of a powder or a lyophilized product which is dissolved when used.

As a preparation of stabilized amrubicin, a preparation incorporated with L-cysteine or a salt thereof has been known (e.g., Japan Patent Gazette No. 2,603,480, the corresponding U.S. Pat. No. 6,376,469).

DISCLOSURE OF INVENTION

On the other hand, it is known that the representative degradation products of amrubicin are a desacchairified compound of the following formula (2) (referred to as "desaccharified compound (2)"):

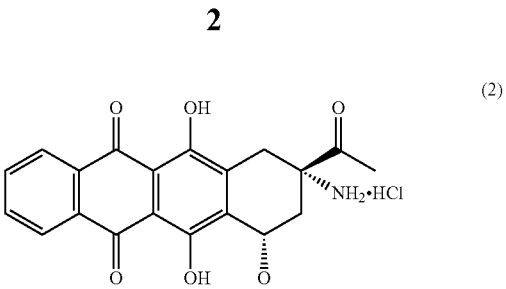

(2)

and a deaminated compound of the following formula (3) (hereinafter, referred to as "deaminated compound (3)"):

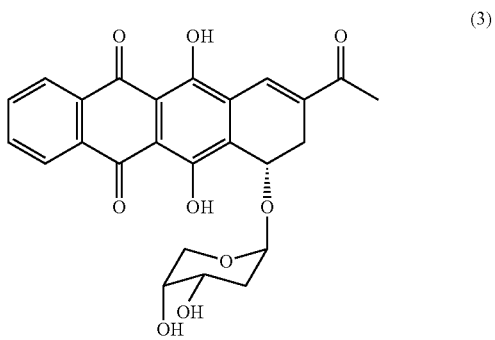 [SMILES: CC(=O)C1=Cc2c(O)c3c(c(O)c2[C@@H](OC2CC(O)C(O)CO2)C1)C(=O)c1ccccc1C3=O]

(3)

and it has been found that these degradation products tend to increase during the production procedures or the storage of amrubicin preparations. From a viewpoint of guarantee of quality as medicaments, it is extremely important to suppress the increase of these degradation products over a long period of time, and it has been desired to develop a method for further stabilizing amrubicin preparations.

In addition, there are anthracycline anticancer agents being clinically used other than amrubicin. Commercially available anthracycline anticancer agents other than amrubicin have a structure having a hydroxy group at the 9-position of the anthracycline nucleus as shown below, while amrubicin has an amino group at the 9-position, and there is a structural difference between amrubicin and the other anthracycline anticancer agents. Therefore, only amrubicin generates a deaminated compound (3) as a degradation product, which leads to the difference of stability from the other anthracycline anticancer agents.

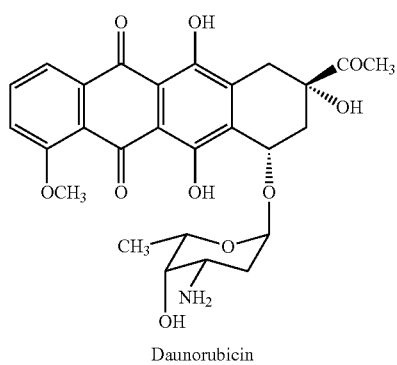

Daunorubicin

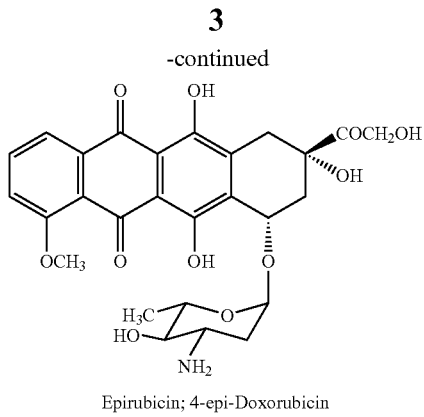

Epirubicin; 4-epi-Doxorubicin

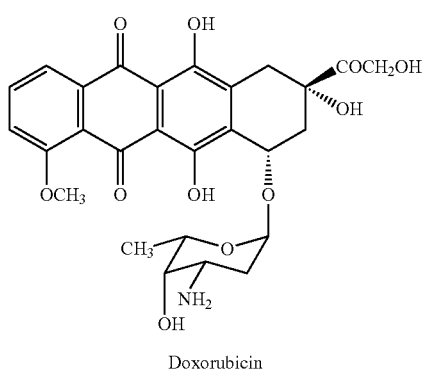

Doxorubicin

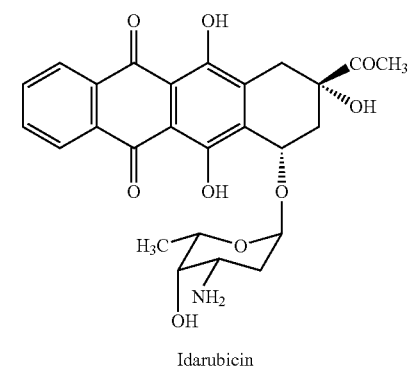

Idarubicin

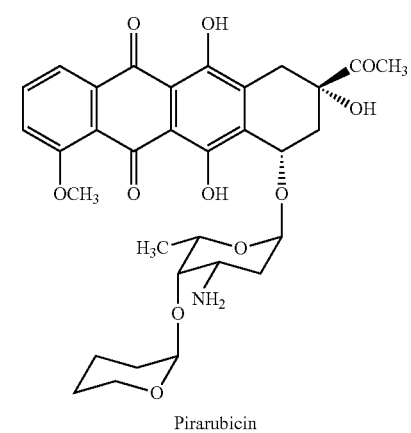

Pirarubicin

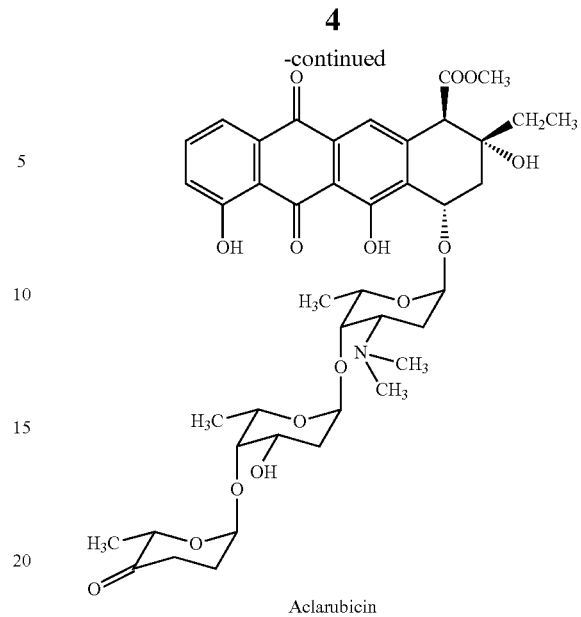

Aclarubicin

Actually, when the anthracycline anticancer agents being sold in Japan (all of them are injections) are dissolved in a distilled water for injection or a physiological saline solution, the pH values thereof are as follows (Drugs (ethical drugs) in Japan, 24 ed., 2001, edited by Japan Pharmaceutical Information Center).

| | |
|---|---|
| Aclarubicin hydrochloride: | 5.0-6.5 |
| Idarubicin hydrochloride: | 5.0-7.0 |
| Epirubicin hydrochloride: | 4.5-6.0 |
| Daunorubicin hydrochloride | 5.0-6.5 |
| Doxorubicin hydrochloride: | 5.0-6.0 |
| Pirarubucin hydrochloride: | 5.0-6.5 |

On the contrary, since amrubicin hydrochloride tends to generate a deaminated compound (3) at a pH value of 3.5 or above, it is unstable at a high pH value as shown in the above anthracycline anticancer agents, and when the lyophilized preparation of amrubicin hydrochloride for clinical administration is dissolved in a physiological saline solution or a 5% glucose injection, the pH value thereof is 2.4 to 3.0.

Namely, as compared to the other anthracycline anticancer agents, the stable pH value for amrubicin hydrochloride is unequally one-sided to the acidic side, and the stable pH value range therefor is narrow. As mentioned above, when the development of a method for stabilizing amrubicin preparations is aimed, it is necessary to consider the conditions being specific to amrubicin, which are different from other anthracycline anticancer agents, since the stability of amrubicin is different from that of the other anthracycline anticancer agents.

As mentioned above, a method of adding L-cysteine or a salt thereof to amrubicin preparations has been known as a method for stabilizing amrubicin preparations. Although the generation of the deaminated compound (3) was suppressed by this method, the desaccharified compound (2) was occasionally increased depending on conditions to be employed.

In order to place amrubicin preparations on market, it was required to study conditions for industrial production methods thereof. Then, the present inventors have intensively studied on a method for further stabilizing said L-cysteine-containing amrubicin preparations, and found the following remarkable findings, and finally have accomplished the present invention.

(1) The water content in the lyophilized amrubicin preparations affect the generation of the desaccharified compound (2), and if the moisture is controlled within a certain definite range thereof, then the generation of the desaccharified compound (2) can be suppressed, by which a lyophilized preparation being stable even in a long-term storage can be obtained.

(2) On the other hand, during the production procedures of the lyophilized preparations, the temperature of the steps in a solution state affects the generation of the degradation product (mainly the deaminated compound (3)), and by conducting said steps at a low temperature sufficient enough, the generation of said degradation product in said steps can be suppressed, and as a result, the contents of the final degradation products (the desaccharified compound (2) and the deaminated compound (3)) in the lyophilized preparations after the long-term storage can be suppressed.

Namely, the present invention provides the following embodiments:

[1] A lyophilized preparation comprising amrubicin or a salt thereof, which is a stabilized preparation being characterized by the following features:
   (1) containing L-cysteine or a salt thereof; and
   (2) having the water content within the preparation in an amount of 0 to about 4% by weight based on the weight of the lyophilized powder.

[2] The stabilized preparation according to the above [1], wherein the water content within the preparation is in the range of 0 to about 3.5% by weight based on the weight of the lyophilized powder.

[3] The stabilized preparation according to the above [1], wherein the water content within the preparation is in the range of about 0.5 to about 3.5% by weight based on the weight of the lyophilized powder.

[4] The stabilized preparation according to the above [1], wherein the water content within the preparation is in the range of about 0.5 to about 2.0% by weight based on the weight of the lyophilized powder.

[5] The stabilized preparation according to any one of the above [1] to [4], wherein the content of L-cysteine or a salt thereof is in the range of about 0.5 to about 250 mg to 100 mg (potency) of amrubicin or a salt thereof.

[6] The stabilized preparation according to any one of the above [1] to [4], wherein the content of L-cysteine or a salt thereof is in the range of about 3 to about 45 mg to 100 mg (potency) of amrubicin or a salt thereof.

[7] The stabilized preparation according to any one of the above [1] to [6], wherein the salt of amrubicin is a hydrochloride thereof.

[8] The stabilized preparation according to any one of the above [1] to [7], wherein the salt of L-cysteine is a hydrochloride thereof.

[9] The stabilized preparation according to any one of the above [1] to [18], wherein L-cysteine or a salt thereof is (1) L-cysteine in an amount of about 5 to about 20 mg, or (2) a salt of L-cysteine in an amount corresponding thereto, to 100 mg (potency) of amrubicin hydrochloride.

[10] The stabilized preparation according to any one of the above [1] to [9], which further comprises an excipient.

[11] The stabilized preparation according to the above [10], wherein the excipient is lactose.

[12] The stabilized preparation according to any one of the above [1] to [11], wherein the salt of amrubicin is crystalline amrubicin hydrochloride showing main peaks at the diffraction angles (2θ) of 6.3°±0.3, 10.1°±0.3, 20.3°±0.3, 26.5°±0.3 and 26.9°±0.3 in the powder X-ray diffraction pattern.

[13] A method for producing a stabilized preparation as set forth in any one of the above [1] to [12], which comprises preparing an aqueous solution containing (a) amrubicin or a salt thereof, and (b) L-cysteine or a salt thereof, sterilizing the resulting solution by aseptic filtration, and followed by lyophilizing the resultant.

[14] A method for producing a stabilized preparation as set forth in any one of the above [1] to [12], which comprises the following Steps (1) to (4):
   (1) preparing an aqueous solution of (a) amrubicin or a salt thereof, and (b) L-cysteine or a salt thereof by dissolving them in water;
   (2) adjusting the pH value of the aqueous solution of the above (1) to about pH 2 to about pH 5;
   (3) sterilizing the aqueous solution of the above (2) by aseptic filtration;
   (4) lyophilizing the aqueous solution obtained in the above (3).

[15] The method according to the above [14], wherein the salt of amrubicin is a hydrochloride thereof.

[16] The method according to the above [14] or [15], wherein the salt of L-cysteine is a hydrochloride thereof.

[17] The method according to any one of the above [14] to [16], wherein the pH value is adjusted into the range of about pH 2.0 to about pH 3.5 in Step (2).

[18] The method according to any one of the above [14] to [16], wherein the pH value is adjusted into the range of about pH 2.2 to about pH 3.0 in Step (2).

[19] The method according to any one of the above [14] to [18], wherein Steps (1) to (3) are conducted at a temperature of about 15° C. or below.

[20] The method according to any one of the above [14] to [18], wherein Steps (1) to (3) are conducted at a temperature of about 10° C. or below.

[21] The method according to any one of the above [14] to [20], wherein the salt of amrubicin is crystalline amrubicin hydrochloride showing main peaks at the diffraction angles (2θ) of 6.3°±0.3, 10.1°±0.3, 20.3°±0.3, 26.5°±0.3 and 26.9°±0.3 in the powder X-ray diffraction pattern.

[22] A method for producing a stabilized lyophilized preparation of amrubicin, which comprises the following Steps (1) to (4):
   (1) preparing an aqueous solution containing amrubicin hydrochloride, L-cysteine in an amount of about 5 to about 20 mg (or a corresponding amount of a salt of L-cysteine) to 100 mg potency of amrubicin hydrochloride, and an excipient;
   (2) adjusting the pH value of the aqueous solution of the above (1) into the range of about pH 2.0 to about pH 3.5;
   (3) sterilizing the aqueous solution of the above (2) by aseptic filtration;
   (4) lyophilizing the aqueous solution obtained in the above (3) to give a lyophilized preparation wherein the water content within the preparation is in the range of 0 to about 4% by weight based on the weight of the lyophilized powder.

[23] The method according to the above [22], wherein the excipient is lactose.

[24] A chemotherapeutic agent for cancers which comprises a stabilized preparation as set forth in any one of the above [1] to [12].

[25] A chemotherapeutic agent for cancers which comprises a lyophilized preparation as set forth in any one of the above [13] to [23].

BRIEF DESCRIPTION OF DRAWING

FIG. 1 shows the generated amount of the desaccharified compound (2), which is one of the degradation products, when the lyophilized preparations of amrubicin containing various amounts of water are subjected to the stability test at 40° C. (Experiments 2 and 3). The abscissa axis indicates the elapsed period (month). Each kinked line indicates the data of the following preparations, respectively.

●: Water-addition Preparation B of Experiment 2 (the water content at the start=5.0%)

○: Water-addition Preparation A of Experiment 2 (the water content at the start=3.5%)

Δ: Blank of Experiment 2 (Preparation without water-addition) (the water content at the start=1.3%)

x: Preparation obtained in Example 2 (the water content at the start=0.7%)

♦: Preparation obtained in Example 3 (the water content at the start=0.6%)

BEST MODE FOR CARRYING OUT THE INVENTION

The present invention will be illustrated in more detail below.

In the present specification, unless otherwise specified, the "water content" within the preparation is expressed in percentage by weight based on the weight of the lyophilized powder. The contents of the desaccharified compound (2) and the deaminated compound (3) are expressed in percentage by weight based on the weight of amrubicin.

The water content within the preparation is in the range of 0 to about 4% by weight, preferably in the range of 0 to about 3.5% by weight, more preferably in the range of about 0.5 to about 3.5% by weight, and further, the content of moisture in the range of about 0.5 to about 2.0% by weight is effective.

The acid to be utilized for forming a salt of amrubicin includes, in addition to hydrochloric acid, hydrobromic acid, citric acid, tartaric acid, lactic acid, fumaric acid, maleic acid, methanesulfonic acid, etc. With respect to amrubicin hydrochloride, it is more preferable to use β-type crystalline amrubicin hydrochloride, which is more stable crystalline form, i.e., crystalline amrubicin hydrochloride showing main peaks at the diffraction angles (2θ) of 6.3°±0.3, 10.1°±0.3, 20.3°±0.3, 26.5°±0.3 and 26.9°±0.3 in the powder X-ray diffraction pattern (cf., Japan Patent Gazette No.2975018). The powder X-ray diffraction pattern can be measured with an X-ray powder diffractometer (RINT2500V; manufactured by RIGAKU CORPORATION) using 1.541 Å of Cu·Kα.

The salt of L-cysteine is usually a hydrochloride, and as other salts thereof, a sulfate, etc. may be exemplified. L-Cysteine or a salt thereof may be in the form of a solvate thereof such as hydrate, and the preferable one is L-cysteine hydrochloride monohydrate.

The amount and the method for adding L-cysteine or a salt thereof may not be necessarily specified, but from a viewpoint of the relationship with the degree of stabilization of amrubicin or pharmacological activities of additives, L-cysteine or a salt may be added in an amount of about 0.5 to about 250 mg, preferably in an amount of about 3 to about 80 mg, more preferably in an amount of about 3 to about 45 mg, to 100 mg (potency) of amrubicin hydrochloride. More preferably, it is appropriate to add L-cysteine in an amount of about 5 to about 20 mg, or a salt of L-cysteine in an amount corresponding thereto, to 100 mg (potency) of amrubicin hydrochloride. Herein, the "salt of L-cysteine in an amount corresponding thereto" means that the L-cysteine contained in said salt is equivalent to the amount of L-cysteine as defined above. For example, the amount corresponding to L-cysteine (121.2 mg) of L-cysteine hydrochloride is 157.6 mg, and in like wise, the amount corresponding thereto of L-cysteine hydrochloride monohydrate is 175.6 mg. When L-cysteine hydrochloride monohydrate is used as a salt of L-cysteine, the amount corresponding to "L-cysteine in the range of about 5 to about 20 mg" of L-cysteine hydrochloride monohydrate is in the range of about 7.2 to about 29 mg.

Taking the features of amrubicin into consideration, it is preferable to control the pH value into the range of about pH 2 to about pH 5, preferably into the range of about pH 2.0 to about pH 3.5, more preferably into the range of about pH 2.2 to about pH 3.0, and especially preferably into the range of about pH 2.4 to about pH 3.0. In this case, a base and/or an acid may be added thereto as a pH adjuster.

Further, the base being capable to be used as a pH adjuster in the present invention may be, for example, a hydroxide of an alkali metal (e.g., sodium, potassium, etc.), a hydroxide of an alkaline earth metal (e.g., magnesium, calcium, etc.), or an alkali metal salt of a weak acid, etc. The alkali metal salt of a weak acid includes, for example, carbonates, hydrogen carbonates, phosphates, hydrogen phosphates, dihydrogen phosphates, citrates, hydrogen citrates, dihydrogen citrates, etc., and they may be in the form of a hydrate, and they may be used by mixing two or more of these salts.

Examples of the base being capable to be used as a pH adjuster are sodium hydroxide, potassium hydroxide, sodium carbonate, sodium hydrogen carbonate, potassium carbonate, potassium hydrogen carbonate, sodium hydrogen phosphate, potassium hydrogen phosphate, sodium phosphate, sodium citrate, sodium dihydrogen citrate, calcium hydroxide, or a hydrate thereof, and further a mixture thereof. Suitable base includes, for example, sodium hydroxide, potassium hydroxide, sodium carbonate, sodium hydrogen carbonate, potassium carbonate, etc. More preferable ones are sodium hydroxide or potassium hydroxide.

In the present invention, the acid being capable to be used as a pH adjuster includes, for example, hydrochloric acid, sulfuric acid, etc.

Additives such as excipient, etc., which can be conventionally added as an additive for pharmaceutical preparations, may be added to the lyophilized preparation of the present invention, if necessary. The excipient includes, for example, lactose, sucrose, palatinose, glucose, maltose, fructose, mannitol, erythritol, xylitol, maltitol, inositol, dextran, sorbitol, albumin, and a mixture thereof. Preferable excipients are lactose, sucrose, glucose, maltose, fructose, mannitol, xylitol, inositol, dextran, and a mixture thereof, and more preferably, lactose, mannitol, and a mixture thereof are exemplified.

The method for producing the lyophilized preparations comprises, for example, dissolving amrubicin or a salt thereof, L-cysteine or a salt thereof, and if necessary, an excipient, etc. in a distilled water for injection, adjusting the pH value of the obtained solution with a trace amount of a base and/or an acid, sterilizing the resultant solution by aseptic filtration and filling it into a vial container, then subjecting the vial to lyophilization to give a power preparation. For injections, the powder preparation thus obtained is stored as it stands, and dissolved in water when used and injected. In order to avoid the degradation in a solution sate, the steps from the dissolution to just before the lyophilization should be preferably conducted at a temperature of about 15° C. or below, more preferably at a temperature of about 10° C. or below.

The lyophilized stable preparation comprising amrubicin or a salt thereof of the present invention may be used as a chemotherapeutic agent for cancers in the treatment of various cancerous diseases. The cancer to be treated by the present preparation may not be necessarily specified, and may include cancerous diseases including hematopoietic tumors, solid tumors, etc. With respect to a dosage of the present preparation to be used in the treatment of human and when it is administered intravenously, the present preparation is administered, for example, in an amount of about 5 to 300 mg per day, preferably in an amount of 20 to 250 mg per day, more preferably in an amount of 35 to 160 mg per day, per square meter body surface area, by continuous infusion. As the administration schedule thereof, the present preparation is given as a single dose, or as everyday medication once a day for 3 days, etc.

EXAMPLES

The present invention will be illustrated by Examples below, but the present invention should not be construed to be limited thereto. In the following Examples and Experiments, β-type crystalline amrubicin hydrochloride was used, which was prepared by the method disclosed in Japan Patent Gazzete No. 2975018.

The water content within the lyophilized preparations may vary according to conditions such as degree of vacuum, temperature and drying period during the lyophilzation procedure, but as shown in Examples and Experiments, the water content within the lyophilized preparations may be controlled by controlling these conditions.

Example 1

To amrubicin hydrochloride (20 mg potency) were added L-cysteine hydrochloride monohydrate (3.2 mg) and lactose (50 mg) as an excipient, and the resultant was dissolved in a distilled water for injection in such a manner that a concentration of amrubicin hydrochloride of the solution was adjusted to 5 mg/ml. The pH value of the solution was slightly adjusted into about pH 3 with a trace amount of sodium hydroxide and hydrochloric acid, and the resulting solution was sterilized by aseptic filtration, and each 10 ml thereof was put into a vial container (capacity: 18 ml). The vial containers were put into a lyophilizer, and sufficiently frozen. Then, the moisture in the vials was sublimated and dried at 20° C. for 49 hours while the temperature and the degree of vacuum were controlled so that the lyophilized cake was not molten, and the vials were sealed with rubber plugs and cap-seals to give a stable lyophilized preparation (the water content: 0.9%).

Example 2

To amrubicin hydrochloride (20 mg potency) were added L-cysteine hydrochloride monohydrate (3.2 mg) and lactose (50 mg) as an excipient, and the resultant was dissolved in a distilled water for injection in such a manner that a concentration of amrubicin hydrochloride was adjusted to 5 mg/ml. The pH value of the solution was slightly adjusted to about pH 3 with a trace amount of sodium hydroxide and hydrochloric acid, and the resulting solution was sterilized by aseptic filtration, and each 4 ml thereof was put into a vial container (capacity: 18 ml). The vial containers were put into a lyophilizer, and sufficiently frozen. The moisture in the vials was sublimated and dried at 20° C. for 24 hours while the temperature and the degree of vacuum were controlled so that the lyophilized cake was not molten, and further, the vials were dried at 40° C. for 8 hours, and sealed with rubber plugs and cap-seals to give a stable lyophilized preparation (the water content: 0.7%).

Example 3

To amrubicin hydrochloride (20 mg potency) were added L-cysteine hydrochloride monohydrate (3.2 mg) and lactose (50 mg) as an excipient, and the resultant was dissolved in a distilled water for injection in such a manner that a concentration of amrubicin hydrochloride was adjusted to 5 mg/ml. The pH value of the solution was slightly adjusted to about pH 3 with a trace amount of sodium hydroxide and hydrochloric acid, and the resulting solution was sterilized by aseptic filtration, and each 10 ml thereof was put into a vial container (capacity: 18 ml). The vial containers were put into a lyophilizer, and sufficiently frozen. The moisture in the vials was sublimated and dried at 20° C. for 37 hours while the temperature and the degree of vacuum was controlled so that the lyophilized cake was not molten, and further, the vials were dried at 40° C. for 12 hours, sealed with rubber plugs and cap-seals to give a stable lyophilized preparation (the water content: 0.6%).

Experiment 1

To amrubicin hydrochloride (20 mg potency) were added L-cysteine hydrochloride monohydrate (3.2 mg) and lactose (50 mg) as an excipient, and the resultant was dissolved in a distilled water for injection. The pH value of the solution was slightly adjusted to about pH 3 with a trace amount of sodium hydroxide and hydrochloric acid, and the resulting solution was sterilized by aseptic filtration, and was put into a vial container (capacity: 18 ml). The vial containers were put into a lyophilizer, and sufficiently frozen. The moisture in the vials was sublimated and dried over a period of 7 hours while the temperature and the degree of vacuum were controlled so that the lyophilized cake was not molten, and the vials were sealed with rubber plugs and cap-seals to give a lyophilized preparation A. Alternatively, the above procedures till the vial filling and freezing were conducted in the same manner as the above, and the moisture in the vials was sublimated and dried over a period of 34 hours while the temperature and the degree of vacuum were controlled so that the lyophilized cake was not molten, and the vials were sealed with rubber plugs and cap-seals to give a lyophilized preparation B. With respect to both of these lyophilized preparations, the water content (measured by Karl Fischer's method) and the degradation products therein (measured by HPLC method) were measured, and the results thereof are shown in Table 1.

TABLE 1

|  | Lyophilized Preparation A | Lyophilized Preparation B |
| --- | --- | --- |
| Lyophilization Conditions | Drying at 20° C. under 20 Pa for 7 hours | Drying at 20° C. under 20 Pa for 15 hours, further at 20° C. under 4 Pa for 19 hours |
| Water content | 12.50% | 0.74% |
| Desaccharified compound (2) | 0.25% | 0.27% |
| Deaminated compound (3) | 0.04% | 0.04% |

As shown in the above data, it was confirmed that the generated amounts of the degradation products such as the desaccharified compound (2) or the deaminated compound (3) do not vary in accordance with the drying period, but the water content significantly differs in accordance with the change of drying period.

Experiment 2

To amrubicin hydrochloride (20 mg potency) were added L-cysteine hydrochloride monohydrate (3.2 mg) and lactose (50 mg) as an excipient, and the resultant was dissolved in a distilled water for injection. The pH value of the solution was slightly adjusted to about pH 3 with a trace amount of sodium hydroxide and hydrochloric acid, and the resulting solution was sterilized by aseptic filtration, and was put into a vial container (capacity: 18 ml). The vial containers were put into a lyophilizer, and sufficiently frozen. The moisture in the vials was sublimated while the temperature and the degree of vacuum were controlled so that the lyophilized cake was not molten, and further sufficiently dried, and the vials were sealed with rubber plugs and cap-seals to give a lyophilized preparation (water content: 1.3%; the desaccharified compound (2): 0.63%; the deaminated compound (3): 0.12%). The obtained lyophilized preparation was subjected to humidity conditioning (water-addition) so that the water content thereof was adjusted to about 3.5% (water-addition preparation A) and about 5% (water-addition preparation B), respectively.

The storage stability test at 40° C. for 3 months or for 6 months was conducted on these preparations, and the water content (measured by Karl Fischer's method) and the degradation products therein (measured by HPLC method) were measured, and the results thereof are shown in Table 2.

TABLE 2

| | | Unit: % | | |
|---|---|---|---|---|
| | Evaluation items | At the start | 40° C.- 3 months | 40° C.- 6 months |
| Blank (preparation without water-addition) | Water content | 1.3 | 1.9 | 2.0 |
| | Desaccharified compound (2) | 0.63 | 2.62 | 4.57 |
| | Deaminated compound (3) | 0.12 | 0.29 | 0.38 |
| Water-addition preparation A | Water content | 3.5 | 3.4 | 3.7 |
| | Desaccharified compound (2) | 0.63 | 3.30 | 5.20 |
| | Deaminated compound (3) | 0.12 | 0.24 | 0.28 |
| Water-addition preparation B | Water content | 5.0 | 4.8 | 4.9 |
| | Desaccharified compound (2) | 0.63 | 10.7 | 16.9 |
| | Deaminated compound (3) | 0.12 | 0.18 | 0.15 |

Experiment 3

With respect to the lyophilized preparations obtained in Example 2 and Example 3, the storage stability test at 40° C. for 3 months or for 6 months was conducted, and the water content (measured by Karl Fischer's method) and the degradation products therein (measured by HPLC method) were measured, and the results thereof are shown in Table 3.

TABLE 3

| | | Unit: % | | |
|---|---|---|---|---|
| | Evaluation items | At the start | 40° C.- 3 months | 40° C.- 6 months |
| Example 2 | Water content | 0.7 | — | 2.2 |
| | Desaccharified compound (2) | 0.37 | 2.36 | 3.73 |
| | Deaminated compound (3) | 0.03 | 0.18 | 0.22 |
| Example 3 | Water content | 0.6 | — | 1.4 |
| | Desaccharified compound (2) | 0.47 | 2.78 | 3.66 |
| | Deaminated compound (3) | 0.03 | 0.18 | 0.22 |

Combining the results of Experiment 2 and Experiment 3, the results thereof are shown in FIG. 1 and FIG. 2.

As shown in the data of the above stability tests, the generated amount of the desaccharified compound (2) after the long-term storage may depend on the water content at the start of the stability test, and the lyophilized preparation wherein the water content within the preparation is controlled within the range of 0 to about 4% by weight showed a remarkably elevated stability as compared to the preparation with a high water content, especially, the generation of the desaccharified compound (2) was well suppressed, and hence, it was confirmed that said lyophilized preparation wherein the water content within the preparation is controlled within the range of 0 to about 4% by weight is stable enough even after the long-term storage. Further, the generated amount of the deaminated compound (3) did not significantly differ, but it was observed that the generated amount of the deaminated compound (3) may tend to slightly increase when the water content is decreased.

Experiment 4

To amrubicin hydrochloride (20 mg potency) in a glass beaker were added L-cysteine hydrochloride monohydrate (3.2 mg) and lactose (50 mg) as an excipient, and the resultant was dissolved in a distilled water for injection. The pH value of the solution was slightly adjusted to about pH 3 with a trace amount of sodium hydroxide and hydrochloric acid, and the resulting solution was put into a temperature-controlled bath at 5° C., 10° C., 15° C. and 25° C. The solution was sampled at the start, 6 hours later, and 24 hours later, and the degradation products therein were measured by HPLC method. The increased amounts of the desaccharified compound (2) and the deaminated compound (3) from those at the start are shown in Table 4.

TABLE 4

| | | Increased amount of desaccharified compound (2) (%) | | | Increased amount of deaminated compound (3) (%) | | |
|---|---|---|---|---|---|---|---|
| No. | Solution temperature | 0 h | 6 h | 24 h | 0 h | 6 h | 24 h |
| 1 | 5° C. | 0.00 | −0.01 | 0.02 | 0.00 | 0.00 | 0.04 |
| 2 | 10° C. | 0.00 | 0.01 | 0.01 | 0.00 | 0.00 | 0.09 |
| 3 | 15° C. | 0.00 | 0.00 | −0.01 | 0.00 | 0.07 | 0.24 |
| 4 | 25° C. | 0.00 | 0.05 | 0.18 | 0.00 | 0.19 | 0.60 |

When the deaminated compound (3) exists at a ratio of about 1% or more, it may cause turbidity when an injection solution is prepared from the lyophilized preparation of amrubicin, and hence, it is necessary to strictly suppress the generated amount thereof into a quite trace amount. On the other hand, as shown in Experiment 2 and Experiment 3, the deaminated compound (3) is generated by bits during the long-term storage of the lyophilized preparations, and hence, it is very important to suppress the amount thereof generated during the formulation procedures in a solution state in order to suppress the generated amount of the deaminated compound (3).

As shown in Table 4, when amrubicin hydrochloride is allowed to stand in a solution state, the generated amount of the deaminated compound (3) therefrom may depend on the temperature of said solution. Therefore, in order to suppress the amount thereof generated during the formulation procedures in a solution state, and finally suppress "the content of the deaminated compound (3) after the long-term storage", it is preferable to conduct the steps in a solution state among the formulation procedures (e.g., Steps (1) to Step (3) of the above [13]) at a temperature of about 15° C. or below, more preferably at a temperature of about 10° C. or below.

The other anthracycline anticancer agents do not have an amino group at the 9-position of the anthracycline nucleus unlike amrubicin, and hence, when producing preparations thereof, it is not necessary to consider the generation of the above deaminated compound, but only desaccharified compounds should be considered during the formulation procedures.

Under the above-mentioned production conditions, the large-scale manufacture of lyophilized preparations of amrubicin may become possible.

INDUSTRIAL APPLICABILITY

By the present invention, the lyophilized preparations of amrubicin, which is useful as a chemotherapeutic agent for cancers, can be obtained, said preparations being stable even after the long-term storage.

The invention claimed is:

1. A method for producing a stabilized lyophilized preparation comprising (1) amrubicin or a salt thereof; and (ii) wherein the water content within the preparation is 0 to 3.5% by weight based on the weight of the lyophilized powder, which comprises the following Steps (1) to (5):

(1) preparing an aqueous solution of (a) amrubicin or a salt thereof, and (b) L-cysteine or a salt thereof by dissolving them in water;

(2) adjusting the pH value of the aqueous solution of the above (1) to pH 2 to pH 5;

(3) sterilizing the aqueous solution of the above (2) by aseptic filtration;

(4) lyophilizing the aqueous solution obtained in the above (3) under conditions for controlling the water content within the preparation so that the water content is in the range of 0 to 3.5% by weight based on the weight of the lyophilized powder and (5) subjecting the preparation to humidity conditions so that the water content is adjusted to a value greater than 0% and up to 3.5%.

* * * * *

UNITED STATES PATENT AND TRADEMARK OFFICE
CERTIFICATE OF CORRECTION

PATENT NO. : 8,445,653 B2
APPLICATION NO. : 10/536397
DATED : May 21, 2013
INVENTOR(S) : Hajimu Hirofuji et al.

Page 1 of 1

It is certified that error appears in the above-identified patent and that said Letters Patent is hereby corrected as shown below:

ON THE TITLE PAGE:

At item (73), correct the identification of the Assignee to read as follows:

--(73) Assignee: Dainippon Sumitomo Pharma Co., Ltd., Osaka-shi (JP)--.

Signed and Sealed this
Fifteenth Day of October, 2013

Teresa Stanek Rea
*Deputy Director of the United States Patent and Trademark Office*